United States Patent [19]

Tahara et al.

[11] Patent Number: 4,555,365

[45] Date of Patent: Nov. 26, 1985

[54] ISOPRENYLIC ACID AMIDE DERIVATIVES

[75] Inventors: Yoshiyuki Tahara, Tsurugashima; Toshihiro Takahashi, Kawagoe; Hiroyasu Koyama, Ageo; Yoshikuni Suzuki, Ohmiya; Masatoshi Yasuda, Kitakyushu, all of Japan

[73] Assignee: Nisshin Flour Milling Co., Ltd., Japan

[21] Appl. No.: 581,345

[22] Filed: Feb. 17, 1984

[30] Foreign Application Priority Data

Feb. 21, 1983 [JP] Japan ................................. 58-26215

[51] Int. Cl.⁴ ........................................ C07C 103/133
[52] U.S. Cl. .................................................. 260/404
[58] Field of Search ........................................ 260/404

[56] References Cited

U.S. PATENT DOCUMENTS 4,456,603 6/1984 Yamatsu et al. ..................... 260/404
4,500,463 2/1985 Sato et al. ............................ 260/406

FOREIGN PATENT DOCUMENTS 0087136 8/1983 European Pat. Off. .

Primary Examiner—Anton H. Sutto
Assistant Examiner—Elizabeth A. Flaherty
Attorney, Agent, or Firm—Abelman, Frayne Rezac & Schwab

[57] ABSTRACT

Compounds of the formula $R_1$—CO—$NH_2$ wherein $R_1$ is

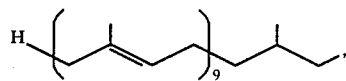

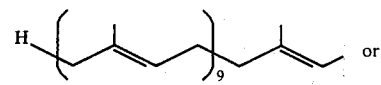 or

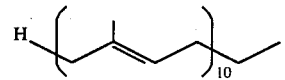

are described. The compounds are useful in the treatment of hypertension and hyperlipidemia.

6 Claims, No Drawings

ISOPRENYLIC ACID AMIDE DERIVATIVES

This invention relates to novel isoprenylic acid amide derivatives represented by the general formula $$R_1-CO-NH_2 \qquad (I)$$

wherein $R_1$ is

,

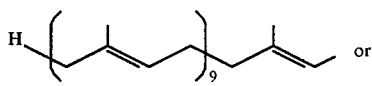 or

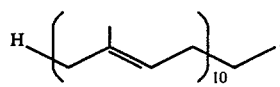

The isoprenylic acid amide derivatives represented by the general formula (I) of this invention are compounds which are useful as therapeutic agents for treatment of hypertension and hyperlipidemia.

For preparation of compounds of the general formula (I) in this invention, all the techniques for formation of amide linkage in ordinary synthesis of peptides are applicable. In more detail according to this invention, the novel isoprenylic acid amide derivatives represented by the general formula $$R_1-CO-NH_2$$

wherein $R_1$ is

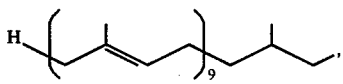,

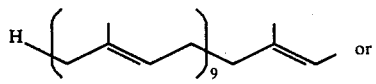 or

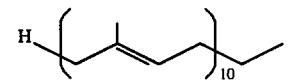

can be manufactured by bringing ammonia to react with (i) acids represented by the general formula $R_1COOH$ wherein $R_1$ is

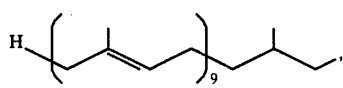,

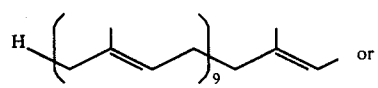 or

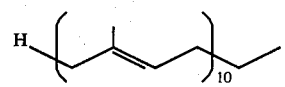

in the presence of condensing agent used for synthesis of peptides, (ii) acid halides represented by the general formula $R_1COX$ wherein $R_1$ is the same as described above and X is a halogen atom, in the presence of a base, or (iii) active esters of an acid represented by the general formula $R_1COOR'$ wherein $R_1$ is the same as described above and $R'$ is an active ester residue used in the synthesis of peptides, or an acid azide selected from a series represented by the general formula $R_1CON_3$ wherein $R_1$ is the same as described above.

Describing the manufacturing process in greater detail, the reaction of ammonia and an acid is carried out for several minutes to tens of hours, preferably for 1 to 30 hours at 50° to 100° C., preferably at 0° to 25° C. in an inert solvent in the presence of a condensing agent when a compound represented by the general formula $R_1COOH$ is used. Ammonia and condensing agent are preferably used in excess of the equimolar proportion of the acid, respectively. Typical compounds used as the condensing agent include N,N-dicyclohexylcarbodiimide and ditolylcarbodiimide. The inert solvents used include halogenated lower aliphatic hydrocarbons, such as chloroform, methylene chloride and trichloroethylene; lower aliphatic lower alkyl esters such as ethyl acetate and butyl acetate; lower aliphatic alcohols such as ethanol, isopropanol and t-butanol; lower fatty acid lower alkyl amides such as N,N-dimethylformamide; lower aliphatic ketones such as acetone and methylethylketone; aromatic hydrocarbons such as benzene and toluene; lower aliphatic alicyclic ethers such as tetrahydrofuran, dioxan and ether; heterocyclic compounds such as pyridine; and nitriles such as acetonitrile.

The reaction with an acid halide is carried out in the presence of a base in an inert solvent at −50° to 100° C., preferably at 0° to 25° C., for several minutes to tens of hours, preferably for 30 minutes to 3 hours, when the compounds represented by the general formula $R_1COX$ are used instead of the compounds represented by the general formula $R_1COOH$. Ammonia is preferably used in excess of the equimolar proportion to the acid halide. The bases used include tertiary amines such as triethylamine and dimethylaniline and heterocyclic compounds such as pyridine. The inert solvents used include ordinary organic solvents such as chloroform, methylene chloride, ethyl acetate, N,N-dimethylformamide, acetone, benzene, toluene, tetrahydrofuran, dioxan, ethyl ether, pyridine and acetonitrile.

The reaction with an active ester of acid or an acid azide in an inert solvent is carried out at −50° to 70° C., preferably at 0° to 25° C. for several minutes to tens of hours, preferably from 30 minutes to 20 hours when the compounds represented by the general formula $R_1COOR'$ and general formula $R_1CON_3$ are used instead of the compounds represented by the general formula $R_1COOH$. Ammonia is preferably used in excess of the equimolar proportion to the active ester of acid and acid azide, respectively. The active ester groups of active esters of acid include p-nitrophenyl group, pentachlorophenyl group, succinimide group, phthalimide group, and so forth. All of the inert solvents mentioned above can be utilized for the reaction.

The desired isoprenoid acid amide derivatives are obtained when the reaction mixture after the end of the reaction described is condensed either with or without filtration, or the mixture is subjected to extraction with solvents such as ethyl acetate, chloroform, hexane, benzene and subsequently purified by means of column chromatography with silica gel or alumina.

This invention is illustrated in further detail in the following examples.

EXAMPLE 1

3,7,11,15,19,23,27,31,35,39-decamethyl-2,6,10,14,18,22,26,30,34,38-tetracontadecaenic acid amide 25 g of 3,7,11,15,19,23,27,31,35,39-decamethyl-2,6,10,14,18,22,26,30,34,38-tetracontadecaenic acid is dissolved in 100 ml of benzene, to which 6.8 ml of 28% sodium methoxide solution is added to form sodium salt, and from which the solvent is removed to dryness under reduced pressure. The dried residue is then dissolved in 100 ml of benzene, added with a trace amount of pyridine, and to which 6 ml of oxalyl chloride is added dropwise at 0° C. with ice bath cooling and stirring. The reaction mixture is kept at 0° C. for 30 minutes, allowed to react at room temperature for 1 hour, and then condensed under reduced pressure. The residue is dissolved in dichloromethylene, and mixed dropwise for 30 minutes with a mixture, cooled below 5° C., consisting of 50 ml of concentrated ammonia liquor, 10 ml of triethylamine and 100 ml of benzene. Stirring is continued further for 2 hours, at room temperature. The reaction mixture is subsequently left standing overnight at room temperature, poured into water, extracted with ethyl acetate, and washed sequentially with water, diluted hydrochloric acid, diluted alkali and water. The ethyl acetate phase is distilled to remove the solvent after desiccation with anhydrous sodium sulfate. The residue is subjected to column chromatography using benzene/ethyl acetate mixture for elution solvent. The product was obtained as an oily substance in light yellow color (yield: 18 g). This oily substance was dissolved in 90 ml of acetone and left overnight in a refrigerator. White crystals deposited were filtered off, dried and thus yielded 13.5 g of desired final product, acid amide derivative. Physical properties of this product are as the following:

m.p.: 46.4°–49.6° C.
Elemental analysis (as $C_{50}H_{81}ON$)

|  | C (%) | H (%) | N (%) |
|---|---|---|---|
| Calculated | 84.32 | 11.46 | 1.97 |
| Found | 84.15 | 11.51 | 1.95 |

IR spectrum ($cm^{-1}$): 3330, 3190, 1663, 1640, 1610.
Mass $M^+$: 712.
NMR spectrum ($\delta$, $CDCl_3$): 5.40–4.80 (br 10H); 2.00 (br-s 36H); 1.60 (br-s 33H).

EXAMPLE 2

3,7,11,15,19,23,27,31,35,39-decamethyl-6,10,14,18,22,26,30,34,38-tetracontanonaenic acid amide 20 g of 3,7,11,15,19,23,27,31,35,39-decamethyl-6,10,14,18,22,26,30,34,38-tetracontanonaenic acid are dissolved in 100 ml of methylene chloride. To this solution, 6.9 g of N,N-dicyclohexylcarbodiimide are added with cooling at 0° C., and stirred for 1.0 hour. Ammonia gas is blown little by little into this solution during an hour. Stirring for 3.0 hours is performed at room temperature after the end of addition of ammonia. Mother liquor is condensed after filtering off N,N-dicyclohexylurea formed. The residue is subjected to silica gel column chromatography using benzene/ethyl acetate mixture for eluting solvent. The desired product was obtained as an oily substance light yellow in color (yield: 12.3 g). This oily substance was dissolved in 50 ml of acetone and left overnight in a refrigerator. The white crystals deposited were filtered off, dried and thus yielded 8.5 g of desired final product, acid amide derivative.

Physical properties of this product are as follows:
m.p.: 47.9°–50.6° C.
Elemental analysis (as $C_{50}H_{83}NO$)

|  | C (%) | H (%) | N (%) |
|---|---|---|---|
| Calculated | 84.09 | 11.71 | 1.96 |
| Found | 84.20 | 11.76 | 1.95 |

IR spectrum ($cm^{-1}$): 3350, 3190, 1650, 1620.
NMR spectrum ($\delta$, $CDCl_3$): 5.4–4.8 (br 9H); 2.00 (br-s 38H); 1.60 (br-s 30H); 0.98 (d 3H).

EXAMPLE 3

5,9,13,17,21,25,29,33,37,41-decamethyl-4,8,12,16,20,24,28,32,36,40-dotetracontadecaenic acid amide 25 g of 5,9,13,17,21,25,29,33,37,41-decamethyl-4,8,12,16,20,24,28,32,36,40-dotetracontadecaenic acid are dissolved in 100 ml of methylene chloride. To this solution, 8.0 g of N,N-dicyclohexylcarbodiimide are added and stirred for 1 hour. 4.5 g of N-hydroxysuccinimide are added and stirred for 3 hours. N,N-dicyclohexylurea thus formed was filtered off; the mother liquor was condensed; and 27.8 g of residue was obtained. The residue was subjected to silica gel column chromatography using hexane/benzene mixture for eluting solvent, and yielded 20.8 g of succinimide ester of 5,9,13,17,21,25,29,33,37,41-decamethyl-4,8,12,16,20,24,28,32,36,40-dotetracontadecaenic acid.

20.8 g of the succinimide ester described above is dissolved in 100 ml of tetrahydrofuran, into which ammonia gas is blown little by little during 1.0 hour. After the end of ammonia blowing, the solution was stirred at room temperature for 3 hours. 21.1 g of residue was obtained after distilling off the solvent. This residue was purified by silica gel column chromatography using benzene/ethyl acetate mixture for eluting solvent and thus yielded 11.3 g of desired product which is oily and light yellow in color. This oily substance was dissolved in 50 ml of acetone and left overnight in a refrigerator. White crystals which were deposited were filtered off, dried and thus yielded 7.8 g of desired acid amide derivative. Physical properties of this derivative are as the following:

m.p.: 58.6°–61.8° C.
Elemental analysis (as $C_{52}H_{85}NO$)

|  | C (%) | H (%) | N (%) |
|---|---|---|---|
| Calculated | 84.37 | 11.57 | 1.89 |

-continued

| | C (%) | H (%) | N (%) |
|---|---|---|---|
| Found | 84.30 | 11.38 | 1.81 |

IR spectrum (cm$^{-1}$): 3410, 3200, 1660, 1620.

NMR spectrum (δ, CDCl$_3$): 5.40–4.80 (br 10H); 2.00 (br-s 40H); 1.62 (br-s 33H).

Pharmacological tests on the isoprenylic acid amide derivatives according to this invention are described as follows:

(1) Antihypertensive effect on spontaneous hypertension rats (SHR)

Test procedure:

20-week-old SHR were used. Mean blood pressure was 170–180 mm Hg on average. The compound to be tested was suspended in 5% gum arabic and orally administered to SHR. Blood pressure in the descending aorta was measured directly by means of a cannula which had been embedded on the day before testing. Measurements were performed before administration, and at 2, 4, 6 and 24 hours after administration to observe the changes in mean blood pressure.

Compound tested:
3,7,11,15,19,23,27,31,35,39-decamethyl-6,10,14,18,22,26,30,34,38-tetracontanonaenic acid amide [Compound (A)]

Dose: 200 mg/kg

Result: Mean blood pressure of SHR was 176 mm Hg before administration. The value was reduced by 17 mm Hg after the administration. This hypotensive effect was observed even at 6 hours after the administration. Heart rate was not affected at all by this compound.

(2) Antihyperlipidemic effect

Test procedure:

Rats that became hyperlipidemic by being fed 1% cholesterol-contained diet for 10 previous days were used. Compound to be tested was added to make up 0.3% in cholesterol-contained diet, and 10 g of this diet were fed daily to the rats. Total cholesterol, triglyceride and HDL in the serum and total cholesterol in the liver were determined. Antihyperlipidemic effects of the reference compound, clofibrate, were compared with those of the compound tested.

Compound tested: Compound (A)

Result: The compound tested showed biological effects in decreasing cholesterol in the serum and liver, increasing HDL, and decreasing triglyceride in the serum; and the potency was comparable to that of clofibrate.

Based on the pharmacological tests described above, the compound according to this invention is useful in showing antihypertensive effect as well as improving the lipid metabolism. It is promising as a preventive and therapeutic agent against renal, endocrine and essential hypertension as well as a preventive and therapeutic agent against various diseases accompanying arteriosclerosis.

Clinical dosage of the compound according to this invention is generally 200–5000 mg/day and preferably 500–4000 mg/day orally.

What we claim is:

1. An isoprenylic acid amide derivative represented by the general formula $$R_1-CO-NH_2$$

wherein R$_1$ is

[chemical structure with subscript 9]

[chemical structure with subscript 9] or

[chemical structure with subscript 10]

2. An isoprenylic acid amide derivative according to claim 1 which is 3,7,11,15,19,23,27,31,35,39-decamethyl-2,6,10,14,18,22,26,30,34,38-tetracontadecaenic acid amide.

3. An isoprenylic acid amide derivative according to claim 1 which is 3,7,11,15,19,23,27,31,35,39-decamethyl-6,10,14,18,22,26,30,34,38-tetracontanonaenic acid amide.

4. An isoprenylic acid amide derivative according to claim 1 which is 5,9,13,17,21,25,29,33,37,41-decamethyl-4,8,12,16,20,24,28,32,36,40-dotetracontadecaenic acid amide.

5. A therapeutic agent for treatment of hypertension which comprises as an active ingredient an antihypertensive amount of an isoprenylic acid amide derivative represented by the general formula $$R_1-CO-NH_2$$

wherein R$_1$ is

[chemical structure with subscript 9]

[chemical structure with subscript 9] or

[chemical structure with subscript 10]

in a pharmaceutically acceptable carrier.

6. A therapeutic agent for treatment of hyperlipidemia which comprises as an active ingredient an antihyperlipedimic amount of an isoprenylic acid amide derivative represented by the general formula $$R_1-CO-NH_2$$

wherein R$_1$ is

[chemical structure with subscript 9]

-continued
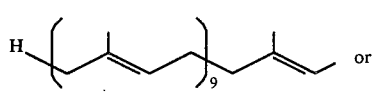 or
-continued
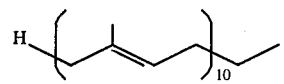
in a pharmaceutically acceptable carrier.
* * * * *